(12) United States Patent
Lögers

(10) Patent No.: US 6,884,897 B2
(45) Date of Patent: Apr. 26, 2005

(54) PREPARATION OF 3,6-DIHYDRO-2H-PYRAN-2-CARBOXYLIC ESTERS

(75) Inventor: Michael Lögers, Wuppertal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/369,156

(22) Filed: Feb. 19, 2003

(65) Prior Publication Data

US 2003/0158430 A1 Aug. 21, 2003

(30) Foreign Application Priority Data

Feb. 21, 2002 (DE) .......................................... 102 07 410

(51) Int. Cl.$^7$ ...................... C07D 311/00; C07D 315/00
(52) U.S. Cl. ..................................... 549/397; 549/425
(58) Field of Search ................................. 549/397, 425

(56) References Cited

PUBLICATIONS

J. Org. Chem USSR (1970 )6, p. 411–416 , E. I. Klimova et al, "Catalytic And Thermal Reactions Of 2,3–Dimethyl–1, 3–Butadiene And Isoprene With Glyoxylic Esters".

Tetrahedron (1993) 49, pp. 4639–4650, Jean Michel Lerestif et al, "Cycloaddition with Stabilized Imidates as Potential Azomethines Ylides : A New Route to 2–Imidazoline and 4–Yliden–5–Imidazolinone.".

Org. Magn, Res.(1983) 21, pp. 94–107, Ernest L. Eliet et al, "Carbon–13 NMR Spectra of Saturated Heterocycles".

J. Chem. Soc., Chem. Commun. (1996), pp. 2373–2374, Anette Graven et al "A highly chemo– and enantio–selective hetero–Diels–Alder reaction catalysed by chiral aluminium complexes".

J. Chem. Soc. Soc. Perkin Trans 1, (1197) pp. 2345–2349, Sulan Yao et al, "Zinc(II–catalysed asymmetric hetero–Diels–Alder reactions of conjugated dienes with glyoxylate".

George Odian "Principles of Poilymerization" pp. 264— Table 3–14.

Johannsen M et al: Asmmetric Hetero Diels–Alder Reactions and Ene Reactions Catalyzed by Chiral Copper(II) Complexes: Journal of Organic Chemistry, American Chemical Society. Easton, US, Bd. 18, Nr. 60, Sep. 1995, Seiten 5757–5762, XPOO1083632 ISSN: 0022–3263 das ganze Dokument.

Robert H et al: "The Carbonyl–Diels–Alder Reaction Catalyzed by Bismuth (III) Chrloride" Tetrahedron Letters, Elsevier Science Bd. 39, Nr. 10, 5. Maerz 1998 (Mar. 5, 1998), Seiten 1161–1164, XPOO4109144 ISSN: 0040–4039 das ganze Dokument.

*Primary Examiner*—Cecilia J. Tsang
*Assistant Examiner*—Raymond Covington
(74) *Attorney, Agent, or Firm*—Diderico van Eyl; Jennifer R. Seng; Jill Denesvich

(57) ABSTRACT

A process is provided for preparing 3,6-dihydro-2H-pyran-2-carboxylic esters via a thermal hetero Diels-Alder reaction of 1,3-dienes with glyoxylic esters without the use of catalysts and stabilizers using a special metering technique.

9 Claims, No Drawings

PREPARATION OF 3,6-DIHYDRO-2H-PYRAN-2-CARBOXYLIC ESTERS

BACKGROUND OF THE INVENTION

1. Field of the Invention

The application relates to a process for preparing 3,6-dihydro-2H-pyran-2-carboxylic esters via a thermal hetero Diels-Alder reaction from 1,3-dienes and esters of glyoxylic acid.

2. Brief Description of the Prior Art

The hetero Diels-Alder reaction of conjugated dienes with carbonyl compounds is one of the fundamental reactions in organic chemistry. Conjugated dienes can in principle be reacted thermally with glyoxylic esters in a hetero Diels-Alder reaction to give 3,6-dihydro-2H-pyran-2-carboxylic esters.

J. Org. Chem. USSR, 1970, 6, 411 discloses the reaction of 2,3-dimethyl-1,3-butadiene or isoprene with ethyl glyoxylate in a thermal hetero Diels-Alder reaction to give the corresponding 3,6-dihydro-2H-pyran-2-carboxylic esters. To this end, diene, ethyl glyoxylate and hydroquinone are mixed on the 500 mmol scale and then heated to 130° C. The 3,6-dihydro-2H-pyran-2-carboxylic esters are obtained on this laboratory scale in yields of 40 to 74%.

According to Tetrahedron 1993, 49, 4639–4650, 10 mmol of ({[(3E)-2-(benzyloxy)-3,5-hexadienyl]oxy}methyl)benzene and other dienes are mixed with butyl glyoxylate and hydroquinone and heated to 130° C. for 18 hours. After workup, cycloadducts are obtained in 60% yield.

Org. Magn. Res. 1983, 21, 94–107 also discloses the preparation of butyl 3,6-dihydro-2H-pyran-2-carboxylates via a thermal Diels-Alder reaction from 1,3-butadiene and butyl glyoxylate on a small scale.

More highly substituted, conjugated dienes generally react at relatively low temperatures and in better yields. For example, reactivity and yield increase in the order 1,3-butadiene<2-methyl-1,3-butadiene<2,3-dimethyl-1,3-butadiene.

In recent times, progress has been made on the route of catalyzed hetero Diels-Alder reactions with glyoxylic esters. The advantage of these methods described, for example, in Tetrahedron Lett. 1998, 39, 1161–1164, J. Chem. Soc., Chem. Commun. 1996, 2373–2374, J. Chem. Soc., Perkin Trans, 1, 1997, 2345–2349 and J. Org. Chem. 1995, 60, 5757–5762 is frequently a relatively low reaction temperature. A disadvantage of the catalyzed syntheses is that expensive (BiCl$_3$, Me—Al[(S)-BINOL], Zn(OTf)$_2$, and toxic (SnCl$_2$, Cu compounds) catalysts which are often difficult to prepare are used which make the process uneconomical. In addition, the removal of the product is distinctly more complicated. For most of these examples, industrial scale reaction is impossible for environmental reasons, since heavy metal wastes (Bi, Sn, Cu) occur.

J. Org. Chem. 1995, 60, 5757–5762 describes the reaction of glyoxylic esters with conjugated dienes catalyzed by a copper(II)-bisoxazoline complex. In this reaction, isopropyl glyoxylate, for example on the 10 mmol scale, is reacted with 5 to 10 equivalents of 1,3-butadiene in dichloromethane in the presence of a catalyst which is formed in situ from Cu(OTf)$_2$ and a chiral oxazolidinone within 5 days to give the corresponding 3,6-dihydro-2H-pyran-2-carboxylic ester. The yield obtained is 55%.

All of the above-mentioned publications on thermally catalyzed reaction of conjugated dienes with glyoxylic esters to give 3,6-dihydro-2H-pyran-2-carboxylic esters have the common disadvantage that the reaction comprises a procedure which (for the purposes of the present application) is referred to as a batch process. In this batch process, all reaction components, i.e. the diene and the glyoxylate (and also the customarily used stabilizer), are initially combined directly at low temperature and mixed with one another and then brought to the required reaction temperature of generally more than 100° C. by heating. These batch processes are only described for performance on the laboratory scale.

However, this procedure, in particular in a reaction on a relatively large scale, is highly questionable for safety reasons, since conjugated dienes, especially 1,3-butadiene, tend to thermally polymerize at elevated temperature and the associated adiabatic temperature increase can lead to thermal decomposition through to explosion of the reaction mixtures.

The strongly exothermic polymerization of 1,3-butadiene sets in, for example, at temperatures above 100° C. with a heat of reaction of about 1350 kJ/kg. Immediately after the polymerization, strongly exothermic decomposition of the polymer occurs from about 295° C. Heat liberated by the decomposition is about 1500 kJ/kg (Odian "Principles of Polymerization" p. 264-Table 3–14. )

These factors lead to a rise in the rate of reaction and an exponential rise in the heat output. The consequence is an exothermic reaction which can no longer be controlled (known as a runaway reaction). This is a barrier in particular to conversion of these reactions to the industrial scale and therefore to an economical utilization of this synthetic route existing in principle.

It is therefore an object of the present invention to provide a process for preparing 3,6-dihydro-2H-pyran-2-carboxylic esters via a thermal hetero Diels-Alder reaction from 1,3-dienes which has no inherent safety problem unlike the existing batch processes and therefore facilitates a synthesis on relatively large scales while at the same time obtaining good yields of the desired product.

SUMMARY OF THE INVENTION

The present application therefore provides a process for preparing 3,6-dihydro-2H-pyran-2-carboxylic esters of the general formula (I)

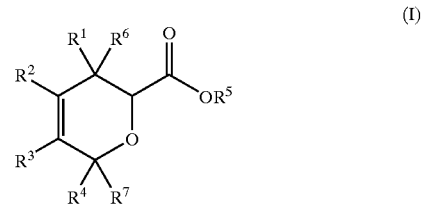

where
- $R^1$, $R^2$, $R^3$ and $R^4$ are the same or different and are each H or a straight-chain or branched $C_1$–$C_7$-alkyl radical,
- $R^5$ is a straight-chain or branched $C_1$–$C_7$-alkyl radical, a phenyl radical or a benzyl radical,
- $R^6$ and $R^7$ are the same or different and are each H or straight-chain or branched $C_1$–$C_3$-alkyl or together form a —(CH$_2$)$_n$-alkylene radical where n=1 or 2, via a thermal hetero Diels-Alder reaction of 1,3-dienes of the general formula (II)

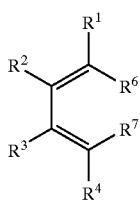

where
R$^1$, R$^2$, R$^3$, R$^4$, R$^6$ and R$^7$ are each as defined for the general formula (I) with compounds of the general formula (III)

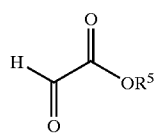

where
R$^5$ is as defined for the general formula (I), characterized in that the process is carried out in the absence of catalysts and stabilizers and the compound of the general formula (III) is initially charged and brought to a temperature of 90–230° C. and the 1,3-diene of the general formula (II) is then added.

DETAILED DESCRIPTION OF THE INVENTION

The compounds of the general formula (II) used in the process according to the invention are preferably those in which the R$^1$, R$^2$, R$^3$ and R$^4$ radicals are the same or different and are each hydrogen, methyl, ethyl, n-propyl, isopropyl, n-butyl, isobutyl, tert-butyl or n-pentyl. R$^6$ and R$^7$ are the same or different and are preferably each hydrogen or methyl.

Preference is given to the R$^1$, R$^2$, R$^3$ and R$^4$ radicals each being hydrogen and R$^6$ and R$^7$ also each being hydrogen. Alternatively, preference is given to one of the R$^1$, R$^2$, R$^3$ and R$^4$ radicals, particular preference to one or two of the R$^1$, R$^2$, R$^3$ and R$^4$ radicals, each being methyl and, at the same time, R$^6$ and R$^7$ being the same or different and each being hydrogen or methyl.

The compounds of the general formula (III) used in the process according to the invention are preferably those in which the R$^5$ radical is methyl, ethyl, n-propyl, isopropyl, n-butyl, isobutyl, tert-butyl, n-pentyl, phenyl or benzyl. Particular preference is given to R$^5$ being methyl, ethyl, n-propyl, isopropyl, n-butyl, isobutyl or tert-butyl.

When R$^5$ is a phenyl or benzyl radical, it may be mono-, di-, tri-, tetra- or pentasubstituted. Examples of substituents of the phenyl or benzyl radical include C$_1$–C$_4$-alkyl, preferably CH$_3$ or C$_2$H$_5$, halogen, preferably fluorine, chlorine or bromine, nitro, —OC$_1$–C$_4$-alkyl, preferably —OCH$_3$ or —OC$_2$H$_5$, and —COOC$_1$–C$_4$-alkyl radicals, preferably —COOCH$_3$ or —COOC$_2$H$_5$.

Compared to the prior art, the process according to the invention is notable for its special metering technique. The compound of the general formula (III) is initially charged and brought to the reaction temperature of 90 to 230° C. Only after that is the 1,3-diene of the general formula (II) added. Customarily, the 1,3-diene is added in such a manner that in each reaction mixture there is only a small excess of 1,3-diene.

Surprisingly, this way of carrying out the process according to the invention allows the presence of expensive, toxic and environmentally damaging heavy metal catalysts to be dispensed with. The use of stabilizers such as hydroquinone, quinone, phenothiazine, picric acid, TBC (p-tert-butylpyrocatechol), TBC (2,6-di-tert-butyl-p-cresol) or 2,6-di-tert-butyl-4-methylphenol is also no longer necessary. According to the prior art, these stabilizers are always used, and in amounts of 0.1 to 5% by weight, based on the 1,3-diene.

It has proven useful to carry out the process according to the invention in such a manner that the compound of the general formula (III), i.e. the glyoxylic ester, is initially charged as such or dissolved in an inert solvent in the reaction vessel. Examples of useful inert solvents include pentane, cyclohexane, hexane, benzene, toluene, xylenes, petroleum ether, chlorobenzene or dichlorobenzenes.

Heating is then effected to the reaction temperature in the range from 90 to 230° C., preferably in the range from 100 to 180° C. Depending on the 1,3-diene used, the range from 120 to 160° C. is also particularly preferred. When 1,3-butadiene is used, reaction temperatures up to a maximum of 180° C. have proven useful.

When low-boiling compounds are used as the reactants in the process according to the invention, i.e. reactants having a boiling point of up to 100° C., in particular 1,3-butadiene, isoprene and 2,3-dimethyl-1,3-butadiene, the reaction vessel used is customarily an autoclave which is pressure-resistant up to at least 25 bar. Once the compound of the general formula (III) has been initially charged, this autoclave is sealed pressure-tight. Depending on the filling level, increasing the temperature to the reaction temperature causes the internal pressure of the closed autoclave to rise to from 2 to 10 bar. For safety reasons, a maximum of 80% of the nominal reactor capacity is customarily filled. In contrast, when exclusively relatively high-boiling reactants are used in the process according to the invention, stirred tanks may also be used: when the boiling points of the reactants are above 100° C., these stirred tanks are used in pressure-tight sealed form. When reactants having boiling points above 200° C. or above the reaction temperature are used, operation may also be effected using an open stirred tank.

Once the reaction temperature is reached, the 1,3-diene of the general formula (II) is then added to the reaction vessel in an amount of 1.0 to 3.0 equivalents, preferably 1.3 to 1.5 equivalents, based on the compound of the general formula (III). When gaseous 1,3-dienes such as 1,3-butadiene are used, they are customarily added from a pressurized tank against the internal pressure which has arisen in the reaction vessel by injecting it in either by means of nitrogen or by means of a metering pump.

The metering time for the addition of the 1,3-diene of the general formula (II) is 3 to 36 hours. The metering time used in each case depends on the 1,3-diene chosen and also on the reaction temperature. In the case of a reaction temperature in the range from 150–180° C., a reaction time of 16 to 6 hours has proven useful. This is suitably followed by a post-reaction of 3 to 24 hours at the above mentioned reaction temperature. Customarily, there is no stirring in the post-reaction.

The reaction mixture is then cooled to 0 to 70° C., preferably to 20 to 40° C., and then withdrawn from the reaction vessel. Customarily, the contents of the reaction vessel are transferred to a distillation plant. In the distillation which is carried out either under atmospheric pressure or else under reduced pressure, solvents, unconverted reactants and secondary components are distillatively removed from the desired 3,6-dihydro-2H-pyran-2-carboxylic ester. If desired, the distillation can be carried out using columns. However, it is also possible to carry it out in the form of a thin-film distillation or via a short-path evaporator.

Owing to its special metering technique, the process according to the invention allows not only catalysts and stabilizers to be dispensed with, but also facilitates a safe performance of the reaction even on the industrial metric ton scale.

At the same time, when the same reactants are chosen, a yield of the desired 3,6-dihydro-2H-pyran-2-carboxylic esters of 30 to 80% is obtained which is higher compared to the existing prior art processes. The particular metering technique allows only a small excess of 1,3-diene to be present in each case in the system, which allows the gradual polymerization of the 1,3-diene to undesired popcorn polymers to be reduced.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Process for preparing 3,6-dihydro-2H-pyran-2-carboxylic esters of the general formula (I)

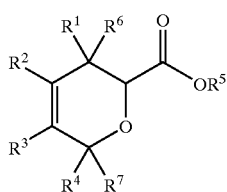

(I)

where $R^1$, $R^2$, $R^3$ and $R^4$ are the same or different and are each H or a straight-chain or branched $C_1$–$C_7$-alkyl radical, $R^5$ is a straight-chain or branched $C_1$–$C_7$-alkyl radical, a phenyl radical or a benzyl radical, $R^6$ and $R^7$ are the same or different and are each H or straight-chain or branched $C_1$–$C_3$-alkyl or together form a —$(CH_2)_n$-alkylene radical where n=1 or 2, via a thermal hetero Diels-Alder reaction of 1,3-dienes of the general formula (II)

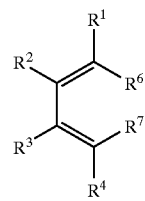

(II)

where $R^1$, $R^2$, $R^3$, $R^4$, $R^6$ and $R^7$ are each as defined for the general formula (I) with compounds of the general formula (III)

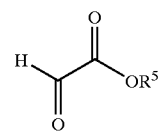

(III)

where $R^5$ is as defined for the general formula (I), comprising conducting the reaction in the absence of catalysts and stabilizers by initially charging the compound of the general formula (III) and heating the charge to a temperature of 90–230° C. and adding the 1,3-diene of the general formula (II).

2. Process according to claim 1, wherein the compounds of the general formula (II) used are those in which the $R^1$, $R^2$, $R^3$ and $R^4$ radicals are the same or different and are each hydrogen, methyl, ethyl, n-propyl, isopropyl, n-butyl, isobutyl, tert-butyl or n-pentyl.

3. Process according to claim 1, wherein $R^1$, $R^2$, $R^3$ $R^4$, $R^6$ and $R^7$ radicals are each hydrogen.

4. Process according to claim 1, wherein the compounds of the general formula (III) used are those in which the $R^5$ radical is methyl, ethyl, n-propyl, isopropyl, n-butyl, isobutyl, tert-butyl, n-pentyl, phenyl or benzyl.

5. Process according to claim 1, wherein the compound of the general formula (III) is initially charged as is or dissolved in an inert solvent.

6. Process according to claim 1, wherein heating is effected to a temperature in the range from 100 to 180° C.

7. Process according to claim 1, wherein the 1,3-diene of the general formula (II) is used in an amount of 1.0 to 3.0 equivalents based on the compound of the general formula (III).

8. Process according to claim 1, wherein the 1,3-diene of the general formula (II) is added in an amount that is effective to produce a small excess of 1,3-diene in the reaction mixture.

9. Process according to claim 1, wherein metering time for the addition of the 1,3-diene of the general formula (II) is 3 to 36 hours.

* * * * *